United States Patent [19]

Elbreder

[11] 4,019,522

[45] Apr. 26, 1977

[54] DENTAL HYGIENE PACKAGE

[76] Inventor: Charles H. Elbreder, 1702 Chase Drive, Fenton, Mo. 63026

[22] Filed: May 5, 1976

[21] Appl. No.: 683,268

Related U.S. Application Data

[63] Continuation-in-part of Ser. No. 541,636, Jan. 16, 1975, abandoned.

[52] U.S. Cl. ................................. 132/90; 132/91
[51] Int. Cl.² ..................................... A61C 15/00
[58] Field of Search ................ 132/92, 89, 90, 91; 424/128, 151–152; 128/335.5

[56] References Cited

UNITED STATES PATENTS

| | | | |
|---|---|---|---|
| 2,128,701 | 8/1938 | Gelinsky | 128/335.5 |
| 2,510,194 | 6/1950 | Thomas | 132/90 |
| 3,337,412 | 8/1967 | Elbreder | 424/128 |
| 3,830,246 | 8/1974 | Gillings | 132/89 |
| 3,830,247 | 8/1974 | Kaphalakos | 132/90 |

*Primary Examiner*—G.E. McNeill
*Attorney, Agent, or Firm*—Koenig, Senniger, Powers and Leavitt

[57] ABSTRACT

A dental hygiene package comprising a container for a body of viscous material including a dental medicament, such as a topical fluoride gel or a gel including a tooth-desensitizing composition. A supply of dental floss is immersed in the body of material thereby to impregnate the floss and adhere to the strands thereof. The container has an orifice through which the medicament-carrying dental floss may be withdrawn. This orifice has a size and shape relative to that of the floss whereby a predetermined and controlled amount of medicament is supplied per length of medicament-carrying floss drawn through the orifice from the container. A cutter is secured to the container for severing the medicament-carrying floss into desired lengths.

12 Claims, 4 Drawing Figures

DENTAL HYGIENE PACKAGE

CROSS-REFERENCE TO RELATED APPLICATION

This application is a continuation-in-part of my co-pending application Ser. No. 541,636, filed Jan. 16, 1975 now abandoned.

BACKGROUND OF THE INVENTION

This invention relates to a dental hygiene package and more particularly to one that will dispense dental floss carrying a dental medicament.

Fluoride therapy for the prevention of dental caries in the dental office and in the home is well known. In the dental office, the patient's teeth are treated with a topical fluoride or phosphatefluoride solution or viscous gel for the prevention of dental caries, as described in my U.S. Pat. No. 3,337,412. Also, fluoride tablets or liquids are prescribed for systemic treatment for control of caries, as described in Elbreder and Ross U.S. Pat. No. 2,967,131. In the home, fluorides have been included in drinking water and toothpaste. Also, mouth rinses and topical gels containing the fluoride ion are available for home therapy.

It is also generally known that there is a high incidence of dental caries and other dental problems which occur at the relatively inaccessible interproximal areas of the teeth. Conventional brushing of the teeth does not effectively reach these regions and mouth rinses and home therapy gels do not always reach those areas. Therefore, the regular and routine use of dental floss for dental prophylaxic and hygiene is widely advocated by the dental profession.

In order to introduce fluoride ions into these interproximal regions, it has been proposed to provide dental floss impregnated with a semisolid dressing in which the fluoride is insoluble and suspended. This impregnated floss as disclosed in U.S. Pat. No. 3,830,246 is then dried for subsequent use. This arrangement, however, entails the expense and difficulties inherent in providing the apparatus and carrying out the processing required in impregnating the floss with the fluoride-containing dressing, drying the impregnated floss and then further processing it into a form for ultimate use and in insuring the convenient supply of desired lengths of the dried treated floss with a properly controlled concentration and evenly distributed amounts of the fluoride medicament.

SUMMARY OF THE INVENTION

Among the several objects of this invention may be noted the provision of a dental hygiene package which supplies or dispenses dental floss carrying a predetermined and controlled amount of dental medicament without any preliminary processing steps; the provision of a dental hygiene package which assures the user of a supply of dental floss freshly coated with medicament and in a viscous form for immediate and effective application to the interproximal surfaces of the teeth; and the provision of such dental hygiene means which may be used for convenient application of fluoride therapy, tooth-desensitizing compositions and other dental medicaments to the interproximal tooth regions.

Briefly, a dental hygiene package of this invention comprises a container and a body of viscous material including a dental medicament therein. A supply of dental floss is immersed in this body of material thereby to impregnate the floss and adhere to the strands thereof. The container is provided with an orifice through which the medicament-carrying dental floss may be withdrawn. The orifice has a size and shape relative to that of the floss whereby a predetermined and controlled amount of medicament is supplied per length of medicament-carrying floss drawn through the orifice. Means are secured to said container for severing the medicament-carrying floss into desired lengths. Other objects and features will be in part apparent and in part pointed out hereinafter.

BRIEF DESCRIPTION OF THE DRAWINGS

Corresponding reference characters indicate corresponding parts throughout the several views of the drawings.

DESCRIPTION OF PREFERRED EMBODIMENTS

Figure 1:
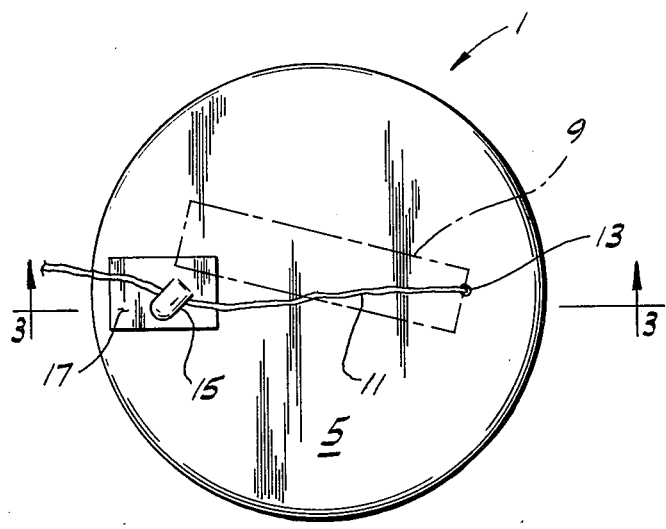
FIG. 1 is a top plan view of a dental hygiene package of the present invention.
Figure 2:
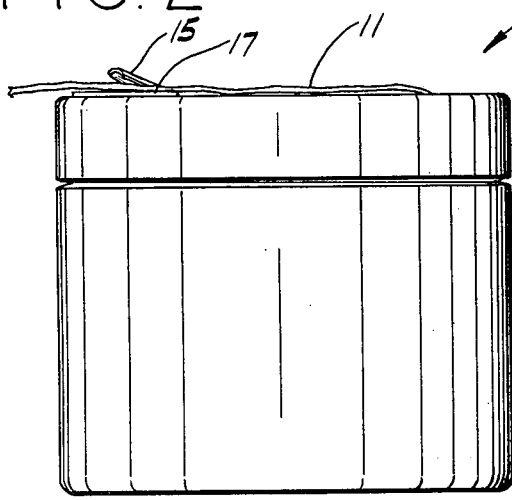
FIG. 2 is a side elevation of the package of FIG. 1.
Figure 3:
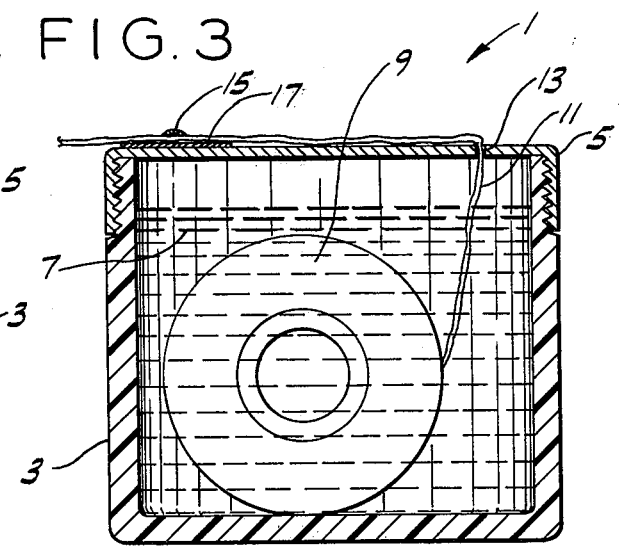
FIG. 3 is a vertical cross section view of the package on line 3—3 of FIG. 1.
Figure 4:
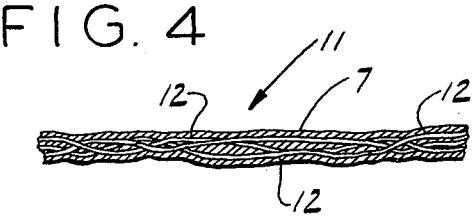
FIG. 4 is greatly enlarged longitudinal sectional view of a length of medicament-carrying floss as dispensed from the dental hygiene package of FIGS. 1–3.

Referring now more particularly to the drawings, a dental hygiene package of the present invention is indicated generally at 1. It comprises a receptacle or container 3 of cup shape with an externally threaded mouth for reception of a screw cover or cap 5. A body 7 of viscous material including a dental medicament is contained in receptacle 3. Immersed in the viscous material 7 is a spool 9 constituting a supply of dental floss 11. The viscous material impregnates the floss 11 and adheres to strands 12 thereof as shown in FIG. 4. Cover 5 has an orifice 13 of a size and shape relative to that of the dental floss so that as the dental floss is drawn therethrough a predetermined and controlled amount of the medicament is supplied per length of medicament-carrying floss dispensed. Secured to cover 5 is a cutter blade 15 struck from a thin metal plate 17 to project angularly therefrom. The integral assembly of blade 15 and plate 17 constitutes means for both severing the floss and temporarily retaining the unsevered portion thereof as illustrated.

More particularly, the material 7 is in the form of a viscous soft paste, preferably a water soluble gel with a dental medicament dissolved therein, with the gel viscosity ranging from about 2500 to about 78,000 centipoises and preferably in the order of between 25,000 and 45,000 centipoises. Viscosity of the gel is typically determined by the use of the wellknown instrument sold under the trade designation "Brookfield Viscometer, Model LV" by Brookfield Engineering Laboratories. One of the standard spindles supplied is selected together with an instrument shear speed or rate that will give at least a 15% deflection on the scale. Exemplary topical fluoride-phosphate gels as described in examples 1, 2, 8 and 12 of U.S. Pat. No. 3,337,412 are desirably used as viscous materials 7. A typical viscosity of 35,000 centipoises (measured at 25° C. with spindle No. 4 at 6 rpm) is quite useful. The volume of gel 7 placed in receptacle 3 is preferably about three times that of the spool 9 of dental floss 11 to provide sufficient medicament material to coat the entire supply of floss as it is dispensed.

Floss 11 is unwaxed, such as can be obtained commercially from John O. Butler Company of Chicago, Ill., and is multistrand, constituted, for example, by over 200 loose filaments 12. The nominal diameter of this floss is 0.007–0.010 inch (0.018–0.025 cm.). The orifice 13 is sized to be somewhat larger than that of the floss. This is an important consideration in that the amount of medicament supplied or carried per given length of floss 11 is predetermined and controlled by the size and shape of this orifice relative to that of the floss and is also a function of the concentration of the therapeutic agent or other dental medicament in the gel. A typical size orifice for the above-mentioned commercial floss is 0.028 inch (0.071 cm.) diameter, although with larger floss this can be increased to 0.0136 inch (0.35 cm.).

The following table shows the assay of fluoride ion available per centimeter length of dental floss where orifice 13 is 0.028 inch and the gel viscosity is 35,000 centipoises:

TABLE

| Percent of F ion in Gel | mg of F ion per cm. of floss |
|---|---|
| 2.00 | 0.220 |
| 1.23 | 0.135 |
| 1.00 | 0.110 |
| 0.50 | 0.055 |
| 0.20 | 0.022 |
| 0.10 | 0.011 |

Preferably the concentration of fluoride ion available per centimeter length of floss is between about 0.01 mg. and 0.2 mg., and more specifically 0.05 mg.

Any of the fluoride compounds dscribed in my U.S. Pat. No. 3,337,412 may be utilized in formation of viscous material 7 and are soluble therein. It will be understood that glycerol may be used to replace up to 30% of the water used in these viscous materials so as to inhibit any tendency of the viscous material to cake at the wiping orifice 13.

The medicament carrying floss 11 as it is withdrawn through the wiping orifice 13 will carry a fresh supply of the gel for immediate and convenient application to the interproximal tooth surfaces as the floss is drawn between the teeth so that the fluoride therapeutic agent in soluble form is immediately available for uptake of the fluoride ion by tooth enamel and dentine.

The dental hygiene package 1 may be used to dispense floss on which is carried viscous material with beneficial dental medicaments other than fluorides. For example, for relief from pain caused by sensitive teeth, the viscous material may incorporate a tooth desensitizing agent. When sensitivity occurs, usually the enamel has eroded away at the base of the teeth in the gingival area exposing the dentine. This problem may be treated in the dental office with a variety of desensitizing agents, for temporary or permanent relief from pain. Pain, associated with sensitive teeth, usually occurs in the interproximal regions of the teeth. There are toothpastes that contain strontium chloride or formaldehyde available for home use for the alleviation of pain in sensitive teeth. However, the tooth brush does not reach the relatively inaccessible interproximal regions. In accordance with this invention, accepted desensitizing therapeutic agents may be applied, not only to the sensitive gingival regions of the teeth, but also to the relatively inaccessible interproximal areas with dental floss carrying a fresh supply of a predetermined and controlled amount of desensitizing medicament per centimeter length of dental floss.

A water-soluble gel having a viscosity of 28,000 centipoises at 25° C. was prepared having the following percentage by weight composition:

| | |
|---|---|
| Strontium chloride ($SrCl_2 \cdot 6H_2O$) | 40% |
| Hydroxyethyl cellulose | 2.3 |
| Glycerol | 7.7 |
| Distilled water | 50 |

The following table illustrates the variation of the amount of medicament carried per centimeter of floss length dispensed where orifice 13 is 0.028 inch and the viscosity is 28,000 centipoises:

TABLE II

| Percent $SrCl_2 \cdot 6H_2O$ in Gel | mg $SrCl_2$ per cm. length of floss |
|---|---|
| 10 | 0.6 |
| 15 | 0.9 |
| 20 | 1.2 |
| 30 | 1.8 |
| 40 | 2.4 |
| 80 | 4.8 |

Preferably the concentration of strontium chloride per centimeter length of floss is between about 0.6 mg and 5.5 mg per centimeter length of floss, and more specifically in the order of 2.5 mg.

Another dental medicament-containing viscous material employed in accordance with this invention has the following percentage by weight composition:

| | |
|---|---|
| Strontium chloride ($SrCl_2 \cdot 6H_2O$) | 14% |
| Polyethylene glycol (Commercially available under the trade designation "Carbowax 400") | 57 |
| Polyethylene glycol (Commercially available under the trade designation "Carbowax 4000") | 8 |
| Ethyl Aminobenzoate ("Benzocaine") | 14 |
| Distilled water | 7 |

The viscosity of this composition is 2,500 centipoises at 25° C. measured with spindle No. 3 at 12 rpm.

Other viscous materials useful in the practice of the present invention include ointment bases, such as water-removable and water-soluble bases as defined in the U.S. Pharmacopeia XVIII, p. 809.

It will be understood that containers or receptacles of widely varying shapes and contours may be used instead of the exemplary one illustrated in the drawings herein, and that medicaments other than the fluoride and tooth-desensitizing agents disclosed may be advantageously employed.

In view of the above, it will be seen that the several objects of the invention are achieved and other advantageous results attained.

As various changes could be made in the above constructions and products without departing from the scope of the invention, it is intended that all matter contained in the above description or shown in the accompanying drawings shall be interpreted as illustrative and not in a limiting sense.

What is claimed is:

1. A dental hygiene package comprising:
   a container;
   a body of viscous material including a dental medicament in said container, said material hving a viscosity in the order of between 2,500 and 78,000 centipoises;
   a supply of dental floss immersed in said body of material thereby to impregnate the floss and adhere to the strands thereof;
   an orifice in said container through which the medicament-carrying dental floss may be withdrawn from said container, said orifice being of a size substantially larger than the cross-section of the floss and having a size and shape relative to that of the floss whereby a predetermined and controlled amount of medicament is supplied per length of medicament-carrying floss drawn through the orifice from said container; and
   means secured to said container for severing the medicament-carrying floss into desired lengths.

2. A package as set forth in claim 1 in which the severing means comprises a cutter blade with means for temporarily retaining the unsevered portion of the withdrawn medicament-carrying floss.

3. A package as set forth in claim 1 in which the body of viscous material is a gel.

4. A package as set forth in claim 3 in which the viscous material is a gel having a viscosity in the order of between about 25,000 and 45,000 centipoises.

5. A package as set forth in claim 3 in which the medicament is one that is soluble in the gel.

6. A package as set forth in claim 1 in which the medicament comprises a fluoride compound soluble in water to provide a source of fluoride ions under acid conditions.

7. A package as set forth in claim 6 in which the concentration of the fluoride compound and the amount of material carried by the floss is such that the concentration of the fluoride ions supplied by the medicament carrying floss is between about 0.01 mg. and 0.2 mg. of fluoride ions per centimeter length dispensed.

8. A package as set forth in claim 7 in which the viscous material is a gel and in which the concentration of the fluoride compound in the gel is such that the gel will have a fluoride ion cencentration of between about 0.1 and 2%.

9. A package as set forth in claim 1 wherein the medicament is a tooth-desensitizing composition.

10. A package as set forth in claim 9 wherein the tooth-desensitizing composition comprises strontium chloride.

11. A package as set forth in claim 10 in which the concentration of the strontium chloride and the amount of material carried by the floss is such that the strontium chloride carried by the floss is between about 0.6 mg. and 5.5 mg. per centimeter length dispensed.

12. A package as set forth in claim 11 in which the viscous material is a gel and in which the concentration of strontium chloride is between about 10 and 80% by weight.

* * * * *